United States Patent [19]

Motta

[11] 4,443,395
[45] Apr. 17, 1984

[54] METHOD FOR PREPARING THIN SECTIONS FOR THE MICROSCOPIC STUDY OF SMALL FRAGMENTS OF ROCK OR DUST, USING A PLATE CONTAINING CELLS

[75] Inventor: Valerio Motta, Milan, Italy

[73] Assignee: AGIP, S.p.A., Rome, Italy

[21] Appl. No.: 413,765

[22] Filed: Sep. 1, 1982

Related U.S. Application Data

[63] Continuation-in-part of Ser. No. 377,940, May 13, 1982, abandoned, which is a continuation of Ser. No. 266,609, May 22, 1981, abandoned, which is a continuation of Ser. No. 781,066, Mar. 24, 1977, abandoned.

[30] Foreign Application Priority Data

Mar. 29, 1976 [IT]  Italy ............................. 21665 A/76

[51] Int. Cl.$^3$ .................... B29C 6/00; B29C 17/12; B29C 23/00; B29D 3/00
[52] U.S. Cl. .................................. 264/117; 264/162; 264/271.1; 264/279; 264/279.1
[58] Field of Search .................... 264/279, 279.1, 117, 264/109, 320

[56] References Cited

PUBLICATIONS

McCall et al., Metallographic Specimen Preparation, Plenum Press, N.Y. (1974) pp. 15–23.
Glanville et al., Injection–Mould Design Fundamentals, Indust. Press, N.Y. (1965), pp. 102–105.
Nichol, Physicochemical Methods of Mineral Analysis, Plenum Press, N.Y., pp. 430–434.

*Primary Examiner*—Willard E. Hoag
*Attorney, Agent, or Firm*—Hedman, Casella, Gibson, Costigan & Hoare

[57] ABSTRACT

This invention relates to a method for preparing thin sections for the microscopic study of small fragments of rock, dust, microfossils or miscellaneous debris, agglomerated into pellets of special characteristics. The method according to the invention comprises the use of a plate of plastic material containing a series of cells which are filled with an agglomerate consisting of rock fragments surrounded with epoxy resin. Said plate is then heated in an oven to a temperature not exceeding 75° C. for some hours in order to accelerate the hardening of the resin and to obtain said pellets.

2 Claims, 4 Drawing Figures

METHOD FOR PREPARING THIN SECTIONS FOR THE MICROSCOPIC STUDY OF SMALL FRAGMENTS OF ROCK OR DUST, USING A PLATE CONTAINING CELLS

The present application is a continuation-in-part of Ser. No. 377,940 filed on May 13, 1982, which is in turn a continuation of Ser. No. 266,609 filed May 22, 1981, which is in turn a continuation of Ser. No. 781,066 filed Mar. 24, 1977, all now abandoned.

This invention relates to a method for preparing thin sections for the microscopic study of smal fragments of rock, dust, microfossils or miscellaneous debris, agglomerated into pellets of special characteristics.

In hydrocarbon exploration for example, petrographic and palaeontological determinations on well cuttings brought to the surface by the mud resulting from drilling are carried out on thin sections.

These are normally obtained by gluing the rock fragments previously chosen from those of larger size on to an object glass using Canada balsam. They are then smoothed by hand (the fragments would separate if automatic machines were used) in successive operations with water and increasingly fine abrasives to obtain a thickness of 2 to 3/100 mm. The preparation of such thin sections is a long and boring operation requiring considerable ability and sensitivity by the operator, such ability and sensitivity being acquired only with time. The pressure of the hand must be regular during the entire operation, otherwise the flakes would become wedge-shaped and would disappear before reaching the required thinness. Prolonged contact of the hands with water leads after some years of this work to forms of arthritis and skin allergies due to the abrasives.

Furthermore, the balsam must be heated to the correct point. If insufficiently heated, it remains soft on cooling, and if excessively heated it becomes fragile.

The sections thus obtained are mostly only just suitable for study, and are rarely excellent. In this respect, for the microscopic examinations to be fruitful, particularly for petrographic determinations, the thin section used must have both of its faces rigorously parallel and a uniform thickness of a maximum of 2 to 3/100 millimeters. At this thickness, a conventional figure for thin petrographic sections, almost perfect transparency is reached for all minerals except those which in practice are opaque at any thickness (these are of limited number in rocks).

Notwithstanding the ability of the operator and the various precautions taken, when the manually prepared thin section is finished the density of the fragments is always very low and their thickness is far from uniform at all points of the section.

The object of the present invention is to provide a practical rapid method as automated as possible for preparing thin sections for the microscopic study of minute fragments of rock or rock dust.

All the aforesaid disadvantages are obviated by the use of a plate as shown in FIG. 1 containing 15 cells for preparing a like number of pellets consisting of rock fragment agglomerates. Said plate is preferably of polypropylene and is constructed by a mold of our design. It preferably measures 158×216 mm and has a thickness of 4 mm. The 15 cells, numbered to facilitate the retrieval of the sample from which the obtained pellet originates, are of truncated pyramid shape as shown in FIG. 2 with a major base of size 21.0×28.0 mm and depth of 3.5 mm. The minor base measures 20.5×27.5 mm and represents optimum useful dimensions for a thin section for petrographic study.

BRIEF DESCRIPTION OF THE DRAWINGS

FIG. 2 is a cross-section through FIG. 1, which is a plan view of the plate. The individual cell is indicated in cross-section by I.

The purpose of the slight flaring of the cells is to facilitate expulsion of the agglomerated pellet once hardened, this expulsion being by slight pressure under the thin base of the cell.

The plates containing the cells may be re-used an infinite number of times and are practically indestructible (they resist inpacts, falls, bending, torsion, etc., and if placed in an oven they withstand temperatures up to 120° C.)

According to the method of the present invention, the fragments are admixed with a suitable epoxy resin, as hereinafter described, and the agglomerate is then placed in the cell. After the fragments have been incorporated into the epoxy resin and the agglomerate placed in the cell, hardening can be accelerated by placing the mold in an oven at a temperature not exceeding 75° C. for a suitable period of time.

Canada balsam had been the agglomerant of choice in the prior art since its refractive index (1.5180–1.5210) approximates that of ordinary glass (*Encyclopedia of Chemical Technology*, Vol. II, publ. 1953 by The Interscience Encyclopedia, Inc, New York). The preferred epoxy resins of the present invention should therefore have a refractive index which approximates that of Canada balsam. As particularly preferred epoxy resins there may be mentioned, for example, p-butylphenyl glycidyl ether, dicyclopentadiene dioxide, diglycidyl ether of bisphenolhexafluoroacetone and phenylglycidyl ether having refractive indices at 25° C., respectively, of 1.5148, 1.5175, 1.5186 and 1.5291. It is to be understood, however, that other epoxy resins having refractive indices at 25° C. in the broad range of about 1.417 and about 1.596 are equally operable. Many epoxy resins falling within the stated refractive index range are commercially available.

It should be pointed out that, while said epoxy resins embrace the rock fragments, they do not stick to the plastic material of the cell.

The pellet thus obtained is very hard and easily extracted from the cell. It may then be fixed with resin on the object glass and introduced into a first automatic diamond wheel machine (e.g. of the BROT multiplaques type) which grinds it to a uniform thickness of 150–100μ (sufficient for micropalaeontological studies).

The pellet reduced in this way is then introduced into an automatic thin section finishing machine (e.g. of the Rockslider BROT type) which can reduce it to a thickness of 20μ.

The thin section obtained in this manner from agglomerate pellets has rigorously parallel faces, and consequently a uniform thickness.

Figure 1:
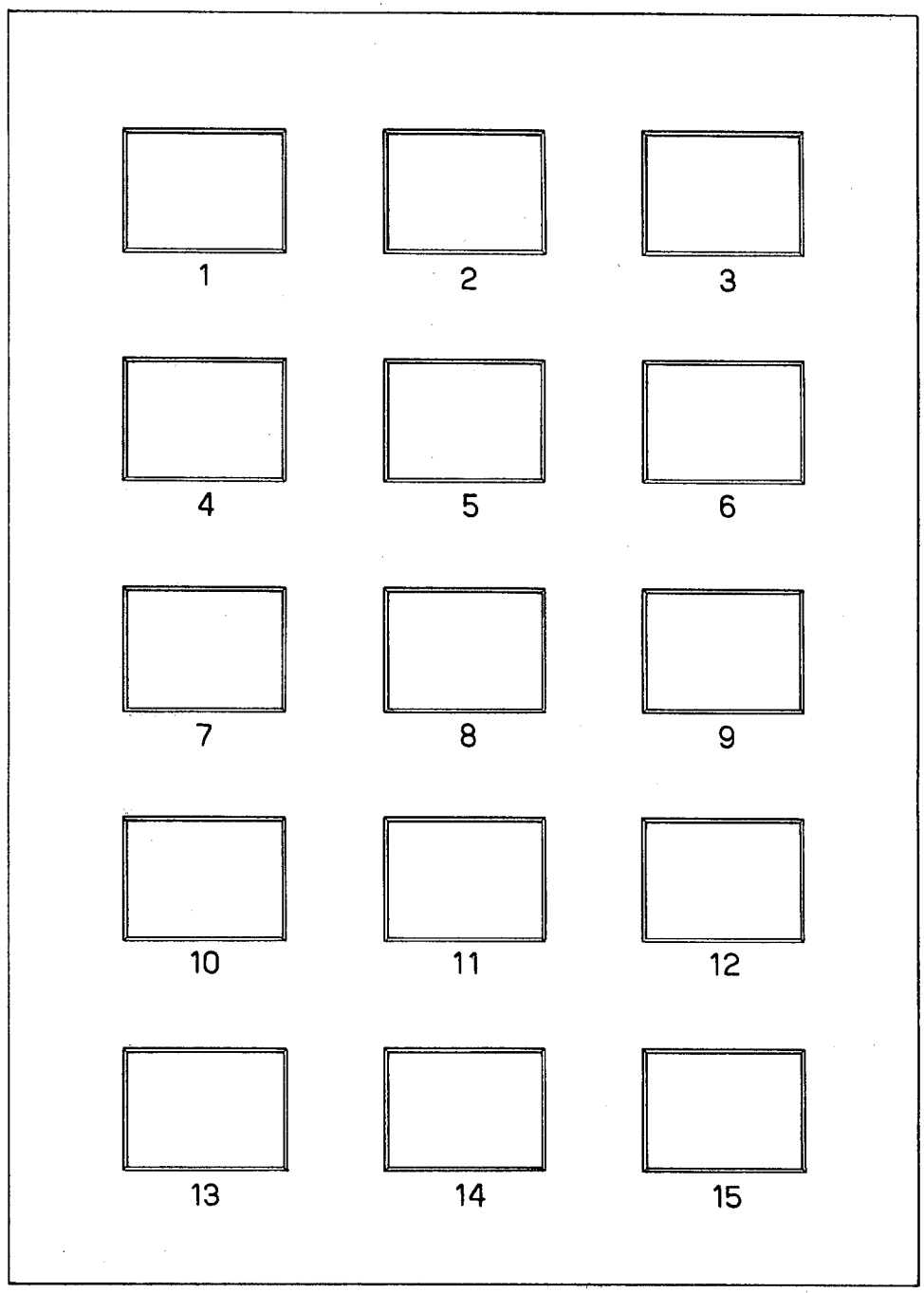
FIGS. 1 and 2 and photographs 3 and 4 are given only by way on non-limiting example.
Figure 2:
Figure 3:
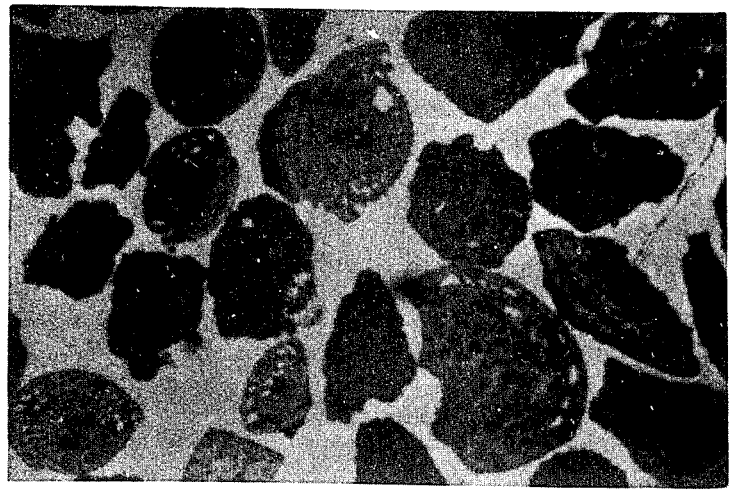
Figure 4:
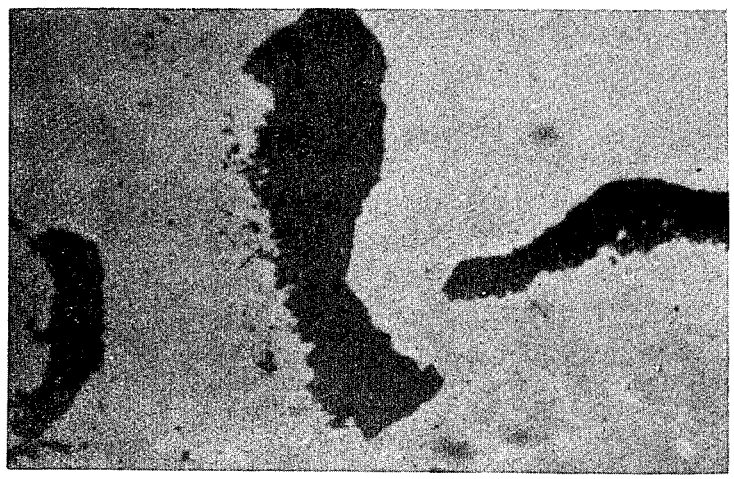

Finally, the most remarkable fact is that at the end of the operation the fragment density in a thin section obtained from agglomerate pellets in accordance with our invention is very high (as shown in FIG. 3, photo 1), and reaches 1 to 25 or more times greater than the density obtained by the preparation method using Canada balsam, as shown in FIG. 4, photo 2 (in said photographs the fragment magnification is 8.4 times).

The cell-containing plate has already been tested and used with greater success in our SGEL laboratories for preparing thin sections of fragments of rock or microfossils both for hydrocarbon exploration and in the mineral industry (uranium minerals), and can certainly open new possibilities and new horizons in other fields (e.g. the spacial field).

Although the present invention has been described with reference to one particular embodiment, the inventive concept is susceptible to numerous other applications.

For example, while polypropylene has been found to be an excellent plastic material for the construction of the plate, other materials, such as polyethylene and polytetrafluoroethylene, can also be used.

Furthermore, without deviating from the spirit of the invention, various modifications may be made to its practical embodiment, all lying within the aforesaid fundamental concepts.

What is claimed is:

1. The method of preparing thin sections for the microscopic study of small fragments of material obtained from well cuttings and the like, said fragments being selected from the group consisting of rock, dust and microfossils, comprising: mixing said fragments with a suitable epoxy resin having a refractive index at 25° C. between 1.47 and 1.596 to form an agglomerate of fragments and resin which will not stick to a plate of plastic material containing a plurality of mold cavities, then forming at least one pellet by placing the agglomerated fragments and resin in at least one of said cavities, each cavity having the shape of a truncated rectangular pyramid with a depth of about 3.5 mm, a major base of 21.0×28.0 mm and a minor base of 20.5×27.5 mm, filling said cells with said pellets, heating said pellets in said cells to a temperature not exceeding 75° C. to cure each pellet, removing the cured pellets from said cells, and thereafter mechanically grinding each of said cured pellets to a uniform thickness in the range of from 50 to 20μ to produce a specimen having optimum transparency with a fragment density in each specimen which is at least from about 1 to 25 times greater than the fragment density heretofore attained.

2. The method of claim 1, wherein said plate is made of a member of a group consisting of polypropylene, polyethylene and polytetrafluoroethylene.

* * * * *